US008666777B2

(12) United States Patent
Schumann et al.

(10) Patent No.: US 8,666,777 B2
(45) Date of Patent: *Mar. 4, 2014

(54) WEB-BASED DATA SUBMISSION FOR NURSING QUALITY INDICATORS

(71) Applicant: The American Nurses Association, Silver Spring, MD (US)

(72) Inventors: Mary Jean Schumann, Brookeville, MD (US); Nancy Dunton, Mission, KS (US); Roma Lee Taunton, Kansas City, MO (US)

(73) Assignee: The American Nurses Association, Silver Spring, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/780,991

(22) Filed: Feb. 28, 2013

(65) Prior Publication Data

US 2013/0179182 A1  Jul. 11, 2013

Related U.S. Application Data

(63) Continuation of application No. 11/048,698, filed on Feb. 3, 2005.

(60) Provisional application No. 60/541,376, filed on Feb. 4, 2004.

(51) Int. Cl.
*G06Q 10/00* (2012.01)
*G06Q 50/00* (2012.01)
*G06Q 50/22* (2012.01)
*G06Q 50/24* (2012.01)

(52) U.S. Cl.
CPC ............... *G06Q 50/22* (2013.01); *G06Q 50/24* (2013.01)
USPC .................................... 705/2; 705/3

(58) Field of Classification Search
CPC ................. G06Q 50/22; G06Q 50/24
USPC ......................................... 705/2–3
See application file for complete search history.

(56) References Cited

U.S. PATENT DOCUMENTS 5,307,262 A * 4/1994 Ertel .................................. 705/2
5,706,441 A * 1/1998 Lockwood ..................... 705/3
5,867,821 A   2/1999 Ballantyne et al.

(Continued)

OTHER PUBLICATIONS

First/Consequent Examination Report as issued for Indian Patent Application No. 923/MUMNP/2006, dated Feb. 28, 2011.

(Continued)

*Primary Examiner* — Sheetal R Rangrej
(74) *Attorney, Agent, or Firm* — Pillsbury Winthrop Shaw Pittman LLP

(57) ABSTRACT

A method for providing comparative reports regarding nursing quality of nursing units at multiple healthcare facilities includes storing information received from multiple healthcare facilities, analyzing the information received from multiple healthcare facilities, obtaining first data associated with a first healthcare facility, transmitting the first data to and storing the first data in the database, obtaining second data associated with a second healthcare facility, and transmitting the second data to and storing the second data in the database. When the first unit type of the first data is a same type as the second unit type of the second data, the method includes performing statistical analysis on the first data and the second data, and outputting results of the statistical analysis.

27 Claims, 14 Drawing Sheets

(56) References Cited

U.S. PATENT DOCUMENTS

| | | | |
|---|---|---|---|
| 6,151,581 A * | 11/2000 | Kraftson et al. ................ 705/3 |
| 6,401,072 B1 | 6/2002 | Haudenschild et al. |
| 6,477,504 B1 * | 11/2002 | Hamlin et al. .............. 705/7.32 |
| 6,556,974 B1 * | 4/2003 | D'Alessandro ............. 705/7.32 |
| 6,611,846 B1 | 8/2003 | Stoodley |
| 6,618,746 B2 | 9/2003 | Desai et al. ................. 709/204 |
| 6,701,345 B1 | 3/2004 | Carley et al. |
| 6,751,651 B2 | 6/2004 | Crockett |
| 7,552,063 B1 * | 6/2009 | McEachern ..................... 705/3 |
| 2002/0059080 A1 | 5/2002 | Kasirer et al. |
| 2002/0087377 A1 | 7/2002 | Rajasenan et al. |
| 2003/0167187 A1 * | 9/2003 | Bua ................................ 705/2 |
| 2004/0243437 A1 * | 12/2004 | Grace et al. ..................... 705/2 |
| 2005/0137929 A1 * | 6/2005 | Frazier et al. ................... 705/9 |
| 2008/0189139 A1 * | 8/2008 | Sachdeva et al. ............... 705/3 |

OTHER PUBLICATIONS

International Search Report as issued for International Application No. PCT/US05/02859, dated Jul. 6, 2005.

Examination Report issued for Canadian Patent Application No. 2,554,026, dated Mar. 5, 2013.

* cited by examiner

200

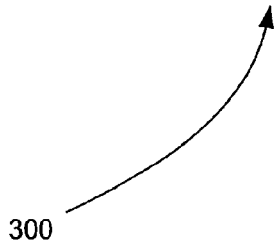

Welcome to the National Database of Nursing Quality Indicators.
Quarterly data entry begins here. In order to accurately track your facility's data to the correct Year and Quarter, Health Care Facility, and Quarterly Reporting Unit, please proceed through a 4-step process to reach the data entry pages.

Step 1 - Select Year and Quarter, then click Continue. Please note that you may go back to any of the previous eight quarters to enter data or make corrections to data submitted in previous quarters. The changes will be reflected in next quarter's report.

Year: 2003     Quarter: Q1 - January, February, March

Continue

Inactivity Notice: When activity ceases for 20 minutes, the site will close. Data saved before that time will be captured and available for editing. You must log back on to restart data entry.

Nursing Care Hours

These are the gross or raw PRODUCTIVE hours worked by nursing staff that had direct patient care responsibilities for greater than 50% of their shift. This category should exclude vacation, sick time, orientation, education leave, or committee time. The hours worked by staff employed directly by the facility are to be reported separately from contract/agency staff.

|  | October | November | December |  |
|---|---|---|---|---|
|  |  |  |  | Save |
| RN Hours - Employee: (Required) | 3211.00 | 2654.00 | 3456.00 | Edit |
| RN Hours - Contract/Agency: (If None, enter Zero) | 0 | 0 | 0 | Edit |
| LPN Hours - Employee: (If None, enter Zero) | 0 | 0 | 0 | Edit |
| LPN Hours - Contract/Agency: (If None, enter Zero) | 0 | 0 | 0 | Edit |
| UAP Hours - Employee: (If None, enter Zero) | 2654.00 | 2145.00 | 2365.00 | Edit |
| UAP Hours - Contract/Agency: (If None, enter Zero) | 0 | 0 | 0 | Edit |

WEB-BASED DATA SUBMISSION FOR NURSING QUALITY INDICATORS

CROSS-REFERENCE TO RELATED APPLICATIONS

This application is a continuation application of U.S. patent application Ser. No. 11/048,698, filed Feb. 3, 2005, which claims the benefit of U.S. Provisional Patent Application Ser. No. 60/541,376 filed Feb. 4, 2004, both of which are herein incorporated by reference in their entireties.

FIELD

Embodiments of the present invention relate to systems and methods for communicating and analyzing nursing quality indicators using networked devices. More particularly, embodiments of the present invention relate to systems and methods for Web-based submission and analysis of nursing quality indicators including pediatric peripheral intravenous infiltration, pediatric pain assessment, and patient assaultive behavior.

BACKGROUND

Exploding health care costs, an aging population, and a shortage of qualified nurses has affected the quality of nursing care in the United States. As a result, it is important to constantly assess the quality of nursing care throughout the country. Traditionally such assessment has been done by individual hospitals or other healthcare facilities. These assessments are typically surveys of the nursing staff. They are conducted through interviews with supervisors or written questionnaires.

These surveys collect information that compares measures of nursing quality with patient outcomes as they relate to nursing care. These measures are known as nursing quality indicators. They are usually monitored over time. They focus on how patients and their conditions are affected by their interaction with nursing staff, how nursing care is delivered, or how staffing patterns affect the quality and quantity of care provided by nurses. Patient outcomes are the end results of the healthcare process. They include adverse outcomes such as pneumonia and pressure ulcers, and positive outcomes such as relief of pain and increase in activities of daily living.

Surveys conducted by individual healthcare facilities result in two problems for facilities and two problems for national health policy. First, while an individual facility may be able to tell if they are improving or deteriorating over time, they will not on their own have the information to determine if they are better or worse than the average facility of their size and type. Second, individual facilities, particularly small facilities, will have insufficient information to identify the relationship between various features of the composition of the nursing work force and patient outcomes and thus will not have an evidence base upon which to design efficient and effective improvements in nursing care.

From a national perspective, if data are collected only by individual facilities, the nation won't have data on trends in nurse staffing and patient outcomes from which to monitor the quality of nursing care, create new policies regarding the nursing shortage, design appropriate guidelines for staffing standards. Further, most individual facilities will not have the resources to develop new indicators of nurse staffing and patient outcomes or to refine existing indicators. New or refined indicators will be needed to expand the assessment of care for all patient populations and to monitor new staffing issues.

The importance of a national, unit-based system for monitoring nursing care and patient outcomes is demonstrated by analysis based on data from such a system that showed that one aspect of nurse staffing, nursing hours per patient day, was related to the patient fall rate on medial and step down units. The association was not present for other measures of nurse staffing, such as skill mix (percentage of hours provided by registered nurses (RNs)) or nurse education and was not present for other unit types, such as critical care or surgical units. This detailed information is more actionable for nurse managers, responsible for the allocation of scare resources among units, than more global hospital-based measures.

A second example from the analysis of an existing system provided information to nurse managers on the quality of the nursing process. Specifically, that among patients who fell, only two-thirds had a prior risk assessment. Of those who had a prior risk assessment, a significant fraction showed the patient not to be at risk for a fall. Finally, of those with a risk assessment and found to be at risk, one-sixth did not receive fall prevention protocol. The outcomes of providing this information to nurse managers could be an extension of the numbers of patients receiving fall risk assessments, improvements in risk assessment tools, and the full implementation of fall prevention protocols among those found to be at risk.

In view of the foregoing, it can be appreciated that a substantial need exists for systems and methods that can advantageously provide for nationwide submission and assessment of both unit-based nursing quality and patient outcome indicators. Further, the system should provide hospitals and policy makers with timely access to comparative, longitudinal benchmarking reports.

SUMMARY

One embodiment of the present invention is a system for surveying nursing quality of nursing units at multiple healthcare facilities connected via a network. A first Web client is connected to the network. The first Web client prompts a staff member of a first nursing unit of a first healthcare facility for a type of data relating to a nursing quality indicator. The first Web client receives a first data element from the staff member of the first nursing unit of the first healthcare facility. The first Web client then transmits a first unit type of the first nursing unit, a first identifier of the first healthcare facility, and the first data element via the network to a Web server.

A second Web client is connected to the network. The second Web client prompts a staff member of the second nursing unit of the second healthcare facility for the same type of data relating to the same nursing quality indicator. The second Web client receives a second data element the staff member of the second nursing unit of the second healthcare facility. The second Web client then transmits a second unit type of the second nursing unit, a second identifier of the second healthcare facility, and the second data element via the network to the Web server. A database stores the first data element along with the first unit type and the first identifier and stores the second data element along with the second unit type and the second identifier.

The Web server transmits the type of data relating to a nursing quality indicator to the first Web client and the second Web client. The Web server receives the first data element, the first unit type, and the first identifier from the first Web client and receives the second data element, the second unit type, and the second identifier from the second Web client. The Web server saves the first data element, the first unit type, the first identifier, the second data element, the second unit type, and the second identifier in the database. If the first unit type and the second unit type are substantially the same type, the Web server performs a comparison of the first data element and the second data element stored in the database and lists results of the comparison based on unit type and healthcare facility. A third Web client receives and displays the results from the Web server, if the first unit type and the second unit type are substantially the same type.

Another embodiment of the present invention is a method for surveying nursing quality of nursing units at multiple healthcare facilities connected via a network. A staff member of a first nursing unit of a first healthcare facility is prompted for type of data relating to a nursing quality indicator via a first Web client connected to the network. A staff member of a second nursing unit of a second healthcare facility is prompted for the same type of data relating to the same nursing quality indicator via a second Web client connected to the network. A first data element is received from the staff member of the first nursing unit via the first Web client, and a second data element is received from the staff member of the second nursing unit via the second Web client. A first unit type of the first nursing unit, a first identifier of the first healthcare facility, and the first data element are received by a Web server, and a second unit type of the second nursing unit, a second identifier of the second healthcare facility, and the second data element are similarly received by the Web server. The first data element along with the first unit type and the first identifier are stored in a database. The second data element along with the second unit type and the second identifier are stored in the database. If the first unit type and the second unit type are substantially the same type, a comparison of the first data element and the second data element stored in the database is performed, the results of the comparison are listed based on unit type and healthcare facility, and the results are transmitted by the Web server to a third Web client for display.

Another embodiment of the present invention is a method for surveying nursing quality of a nursing unit at a healthcare facility connected to a network based on pediatric intravenous infiltration information. A staff member of the nursing unit is prompted for a type of data relating to pediatric peripheral intravenous infiltration via a Web client connected to the network. A data element is received from the staff member via the Web client at a Web server. The data element is stored in a database. A comparison of the data element stored in the database and at least one other data element of the same type of data relating to pediatric peripheral intravenous infiltration received from a second staff member from a second nursing unit of a second healthcare facility connected to the network and stored in the database is performed. A result from the comparison is presented that is accessible through a second Web client connected to the Web server.

Another embodiment of the present invention is a method for surveying nursing quality of a nursing unit at a healthcare facility connected to a network based on pediatric pain assessment information. A staff member of the nursing unit is prompted for a type of data relating to pediatric pain assessment via a Web client connected to the network. A data element is received from the staff member via the Web client at a Web server. The data element is stored in a database. A comparison of the data element stored in the database and at least one other data element of the same type of data relating to pediatric pain assessment received from a second staff member from a second nursing unit of a second healthcare facility connected to the network and stored in the database is performed. A result from the comparison is presented that is accessible through a second Web client connected to the Web server.

Another embodiment of the present invention is a method for surveying nursing quality of a nursing unit at a healthcare facility connected to a network based on patient assaultive behavior information. A staff member of the nursing unit is prompted for a type of data relating to patient assaultive behavior via a Web client connected to the network. A data element is received from the staff member via the Web client at a Web server. The data element is stored in a database. A comparison of the data element stored in the database and at least one other data element of the same type of data relating to patient assaultive behavior received from a second staff member from a second nursing unit of a second healthcare facility connected to the network and stored in the database is performed. A result from the comparison is presented that is accessible through a second Web client connected to the Web server.

BRIEF DESCRIPTION OF THE DRAWINGS

FIG. 3 is an exemplary Web page of an exemplary national database of a nursing quality indicators system used to select the quarter for data entry, in accordance with an embodiment of the present invention.

FIG. 8 is an exemplary Web page of an exemplary national database of a nursing quality indicators system used to review nursing care hours information, in accordance with an embodiment of the present invention.

FIG. 9 is an exemplary Web page of an exemplary national database of a nursing quality indicators system showing how a computer generated number and a countdown number are used in a patient falls data entry module, in accordance with an embodiment of the present invention.

Figure 1:
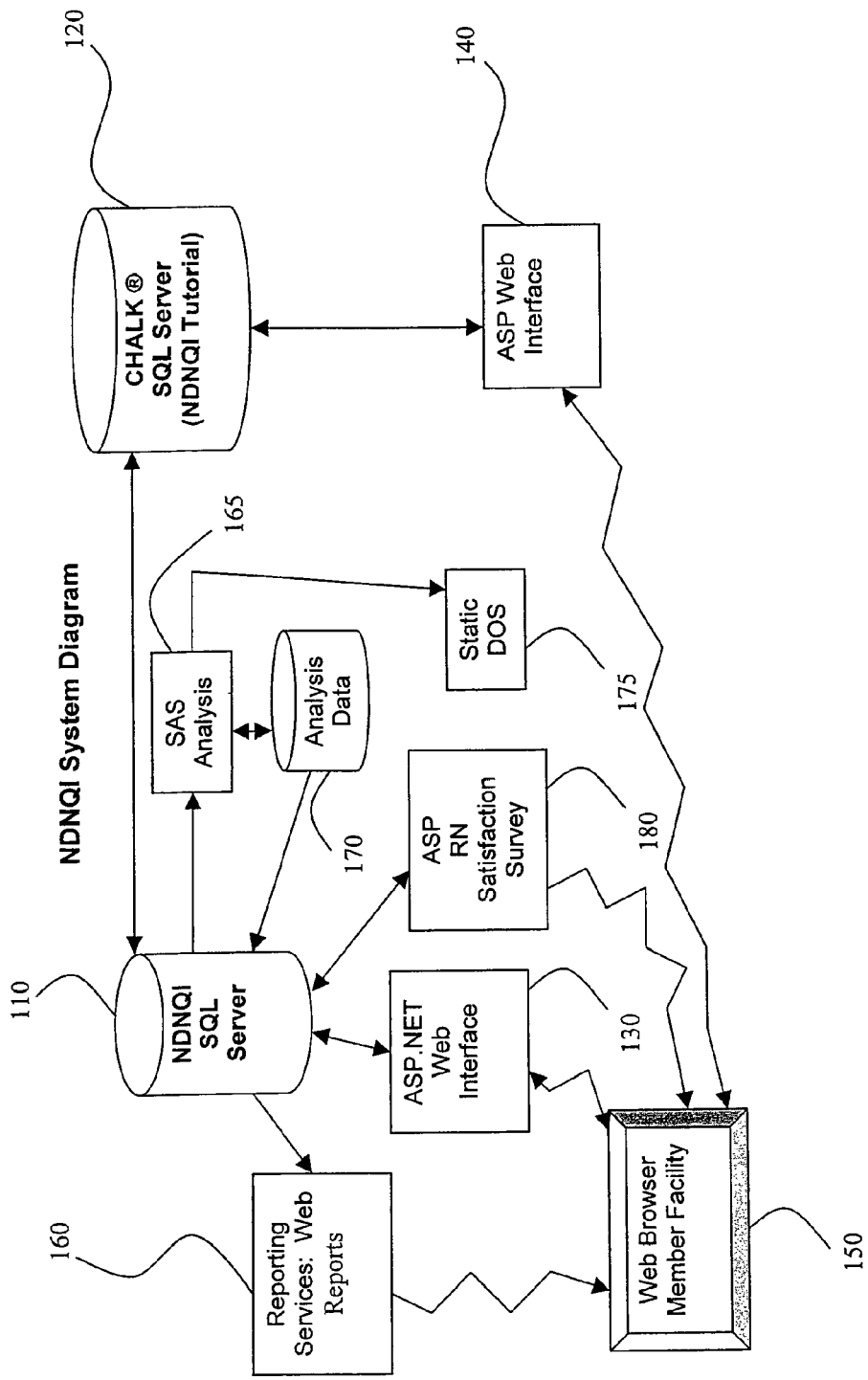
FIG. 1 is a schematic diagram showing an exemplary national database of a nursing quality indicators system, in accordance with an embodiment of the present invention.

Before one or more embodiments of the invention are described in detail, one skilled in the art will appreciate that the invention is not limited in its application to the details of construction, the arrangements of components, and the arrangement of steps set forth in the following detailed description or illustrated in the drawings. The invention is capable of other embodiments and of being practiced or being carried out in various ways. Also, it is to be understood that the phraseology and terminology used herein is for the purpose of description and should not be regarded as limiting.

DETAILED DESCRIPTION

Web-Based System and Method for Surveying Nursing Quality

FIG. 1 is a schematic diagram showing an exemplary national database of a nursing quality indicators (NDNQI) system 100, in accordance with an embodiment of the present invention. NDNQI system 100 is an exemplary system for surveying nursing quality and preferably includes two databases: NDNQI database 110 is used to store survey data, and NDNQI tutorial database 120 is used to store tutorial data.

There are no correct answers to a nursing quality survey. However, proper understanding of nursing quality survey questions is crucial to providing accurate survey answers and meaningful results. Consequently, NDNQI system 100 provides a tutorial for all users entering data. The tutorial first displays information to a user about the questions that will be asked in the survey. The tutorial then requires the user to answer a series of questions about the survey questions. These questions are in the form of a quiz, and there is one correct answer for each quiz question. User's are required to correctly answer the quiz questions before being allowed to provide responses to actual survey questions. Quiz questions are repeated until correct answers are provided. A user of NDNQI system 100 is a staff member of a nursing unit of healthcare facility, for example.

Survey information and responses are stored in NDNQI database 110.

Figure 2:
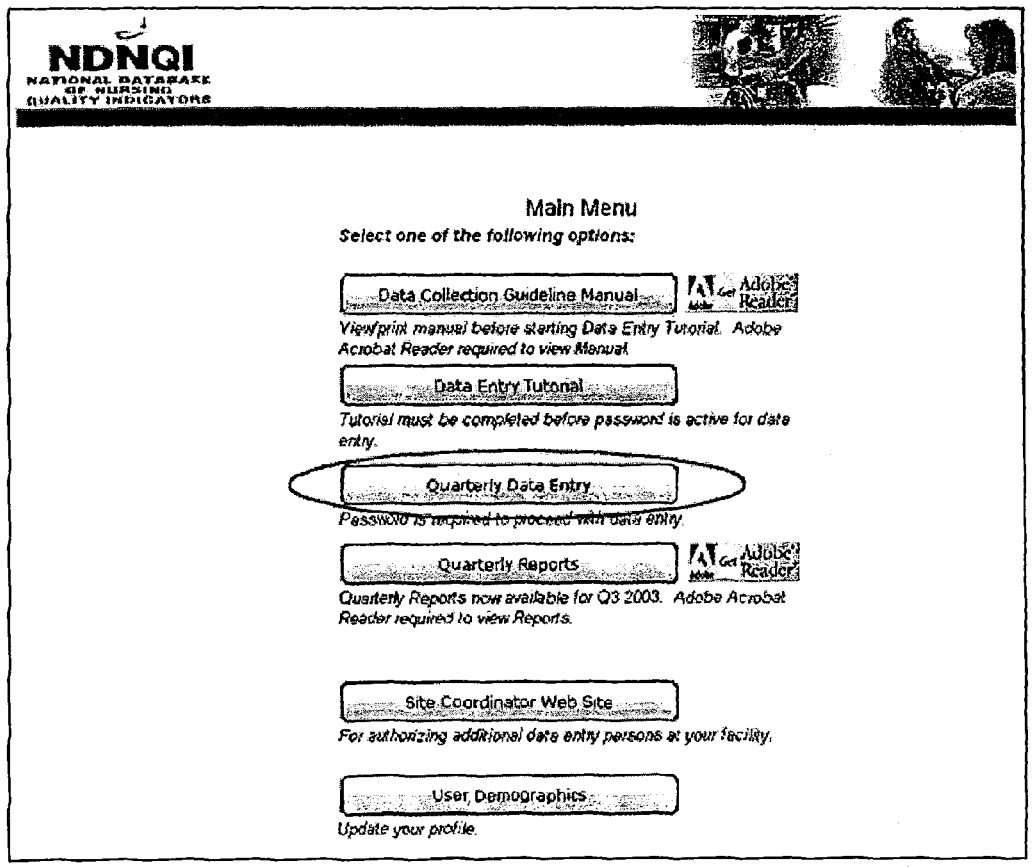
FIG. 2 is an exemplary main menu Web page of an exemplary national database of a nursing quality indicators system, in accordance with an embodiment of the present invention.

Tutorial information and responses are stored in NDNQI tutorial database 120. Web interface 130 provides access to survey information, questions, and responses located in NDNQI database 110. Web interface 140 provides access to tutorial information, questions, and responses located in NDNQI tutorial database 120. One skilled in the art will appreciate that a Web interface 130 and Web interface 140 can be separate Web servers or can be separate Web pages or applications on a single Web server. Users, or members, of NDNQI system 100 access NDNQI system 100 through a Web browser on Web client 150. Web client 150 is preferably located at the user's healthcare facility, but may be located anywhere a Web connection is available. Web client 150 preferably connects to Web interface 140 first. Upon successful completion of the tutorial quiz, Web client 150 connects to Web Interface 130 to allow completion of the survey. FIG. 2 is an exemplary main menu Web page 200 of an exemplary NDNQI system, in accordance with an embodiment of the present invention. The button that is selected to complete a survey is shown circled on Web page 200.

In addition to providing data entry via the Web, NDNQI system 100, in FIG. 1, reports survey results via the Web. Reporting services 160 gather survey results from NDNQI database 110 and present them to a user via Web client 150. One skilled in the art will appreciate that reporting services 160 may include Web services running on one or more Web servers.

Information stored in NDNQI database 110 is periodically analyzed and statistical comparison data is produced. Analysis component 165 extracts the information from NDNQI database 110 and places this information in analysis database 170. Analysis component 165 performs analysis on the information stored in analysis database 170. Analysis component 165 performs this analysis using software from SASS, for example. Statistical comparison data produced by this analysis is returned to NDNQI database 110. This statistical comparison data can also be provided to users in the form of executive summaries, graphs, correlation tables, and maps using data output component 175.

In another embodiment of the present invention, Web interface 180 is provides an interface to a registered nurse (RN) satisfaction survey. RN satisfaction survey information and data is stored in NDNQI database 110. Web interface 180 provides an interactive interface for posing questions to nurses and receiving their responses.

Membership in NDNQI system 100 allows a healthcare facility to compare its nursing unit level patient outcomes, staffing patterns, and nurse satisfaction with other facilities of the same bed size. Two elements are preferably used to categorize a healthcare facility and its nursing units, and to compare or benchmark the healthcare facilities performance with others. The first is bed size and the second is unit type.

Bed size is defined as staffed beds. Bed size is the number of beds available and staffed for patient care, including bassinets. This number may be very different from licensed bed size. Generally, the staffed bed size is close to the average daily census. Staffed beds is the number used to compare the performance of a healthcare facility with others of similar size. The type of nursing unit and bed size of the health care facility are used to categorize the nursing unit and healthcare facility, respectively.

Unit type is used to classify the primary acuity level of a healthcare facility's patients. Each nursing unit is allowed one primary acuity level, excluding occasional overflow of different acuity. It is important to investigate how the staffing numbers are internally reported before enrolling units that will require nursing hours reports. It is important that the method used to record nursing hours be consistent across departments and healthcare facilities. A healthcare facility's payroll department or staffing office may combine staffing numbers for two or more units with differing acuities, which makes separate reports very difficult to obtain. In addition, unit managers should be consulted to verify the typical patient population cared for on each unit. It is crucial to accurately enroll all units with the correct unit type designation so they are properly compared to their peers.

An NDNQI site coordinator serves as the primary point of contact between the NDNQI project and the healthcare facility. The site coordinator is responsible for organizing the data collection processes and communicating with other staff members who assist with data collection, data entry, and report interpretation. The site coordinator receives all official notices by mail or email from the NDNQI project staff including NDNQI membership renewal.

Because the site coordinator is responsible for all data submitted to NDNQI, the site coordinator preferably completes all modules of the tutorial. Each module contains a separate category of nursing quality indicators. However, site coordinators who are responsible for more than one facility need only complete the tutorial one time. Upon completing the modules and passing the quizzes, the tutorial 120 database automatically sends an email to NDNQI system 100 and one of the hospital liaisons for NDNQI system 100 authorizes data entry for the site.

The site coordinator is responsible for authorizing each user after they register and periodically thereafter, i.e., every quarter. For security reasons, this method prevents continuous authorization for data entry by staff that may have left a healthcare facility or changed roles within the healthcare facility.

All users have two sets of records, one in NDNQI database 110 and one in NDNQI tutorial database 120. One is an activated permission and the other is authorization after passing the required quizzes. The site coordinator grants the user permission before the user can study the tutorial. After a user is registered, their name appears in a drop down menu. The site coordinator selects the role the user will have. One person is designated for the role site coordinator, and an unlimited number of staff are assigned to the user role.

The site coordinator also sets the permissions each user is given for data entry. Each user may have more than one permission level. For example, a staff member assigned to enter pressure ulcer data will have three permission levels: active user (required for all users), pressure ulcers, and general overview (required for all users).

All users except the site coordinator are automatically "deactivated" from indicators when the database is temporarily closed for quarterly data processing. The coordinator must re-activate designated user(s) each quarter for their assigned indicator in order for them to enter data. If the user is granted permission for a new data entry role, for example, and the site coordinator enters registered nurse (RN) education data in addition to pressure ulcer data, the user must also pass the quiz for RN education.

The site coordinator is preferably the only user that is allowed to enroll units. The site coordinator preferably does not grant this permission to other users as it can cause duplication of unit enrollment. Trending data on quarterly reports may be difficult to obtain if data meant for one unit is submitted under different unit names.

A user is instructed to initially register as a "new user." A user needs a NDNQI ID code associated with their healthcare facility in order to register. On the registration page, a user provides their name and e-mail address and creates their password. Upon registration, their name is listed on the site coordinator Web page. After they are activated by the site coordinator, users preferably complete a general overview module along with any others that may be required for their assigned data entry role.

Every authorized user is linked by their passwords to all data they have entered or amended. An option to review data includes a report listing the name of the user that last saved the data record. This allows site coordinators to monitor data submitted by each user.

In a preferred implementation, NQNQI system 100 provides member-only web conferencing, which is used by site coordinators and other authorized facility staff to communicate with staff at other sites and to respond to topics posted by NDNQI project staff.

NQNQI system 100 also preferably provides an electronic bulletin board. The site coordinator receives automatic access to the electronic bulletin board and sends an email to NDNQI project staff with the names and email addresses of other staff desiring Bulletin Board access. Each user receives a return email with a login name and password. The password, which can be changed to something more easily remembered upon first logging on, is active for 90 days. "Strong" passwords that contain a combination of letters and numbers or symbols are used. Access is granted for an additional 90 days with each subsequent log on. However, if it has been more than 90 days between log ons, the password expires and access is denied.

The validity of NDNQI data is dependent upon strict adherence to data collection standards. Each indicator is collected in accordance with the definitions and standards set forth in NDNQI tutorial database 120. To ensure the integrity of NDNQI database 110, data is preferably not submitted from alternative sources or via methods that do not adhere to these standards should not be used.

The NDNQI identifier code is a randomly generated code that identifies a healthcare facility in NDNQI database 110 and NDNQI tutorial database 120. Upon receipt of all enrollment materials, the designated site coordinator is sent a welcome letter containing an NDNQI identifier code. This code is used as long as the healthcare facility maintains membership with NDNQI system 100. For security reasons, the NDNQI identifier code is preferably only shared on a "need to know" basis with other staff that are authorized to enter data. It is necessary for a user to use this code to gain access to the logon page and for other staff to register as users.

NDNQI system 100 is preferably available twenty-four hours a day and seven days a week for enrolling units and updating healthcare facility or user information. NDNQI system 100 is closed for a period of a few days when quarterly reports are produced. New data entry and amended data in any of eight previous quarters are typically available between the posting of the quarterly reports and the next quarter's data entry deadline. Data submitted to NDNQI system 100 is based on the calendar quarter and year, not a fiscal quarter and year. The correct year and quarter are selected from drop down menus. FIG. 3 is an exemplary Web page 300 of an exemplary NDNQI system used to select the quarter for data entry, in accordance with an embodiment of the present invention. The year and quarter data entry items are shown circled on Web page 300.

The tutorial, associated quizzes, and web data entry pages have an inactivity timer. If a user remains on the same screen for more than 20 minutes without activity, the session is closed without warning. Any data entered since the last save is lost.

One purpose of the tutorial is to learn about direct data entry into a secure web site. A user has the ability to enter data in increments and to edit previously submitted data. There are a number of automatic error checks in place to reduce typographical errors, to alert the user to missing data, and to alert the user to "outlier" mistakes.

A second data submission method in extensible markup language (XML) format is available for users who have data stored in databases and have programming resources. NDNQI system 100, in FIG. 1, allows members' programmers to enter survey data in a flat file format. Sites have the option of submitting their data exclusively with one method or using a combination of methods.

Figure 4:
FIG. 4 is an exemplary Web page of an exemplary national database of a nursing quality indicators system used to enter healthcare facility information, in accordance with an embodiment of the present invention.

A healthcare facility's identifying information and the healthcare facility's list of enrolled units are preferably maintained in separate databases. FIG. 4 is an exemplary Web page 400 of an exemplary NDNQI system used to enter healthcare facility information, in accordance with an embodiment of the present invention. The architecture is designed in this fashion to comply with Health Insurance Portability and Accountability Act (HIPAA) regulations.

Figure 5:
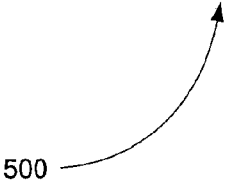
FIG. 5 is an exemplary Web page of an exemplary national database of a nursing quality indicators system used to enter nursing unit information, in accordance with an embodiment of the present invention.

FIG. 5 is an exemplary Web page 500 of an exemplary NDNQI system used to enter nursing unit information, in accordance with an embodiment of the present invention. Nursing unit information is selected from drop down menus, shown circled on Web page 500. This information includes population, specialty, and type, along with the list of eligible indicators, also circled on Web page 500. Each nursing unit is eligible for a specific set of nursing quality indicators based on the unit type designation. The nursing units for which a user is authorized to enter data are displayed for the user.

Figure 6:
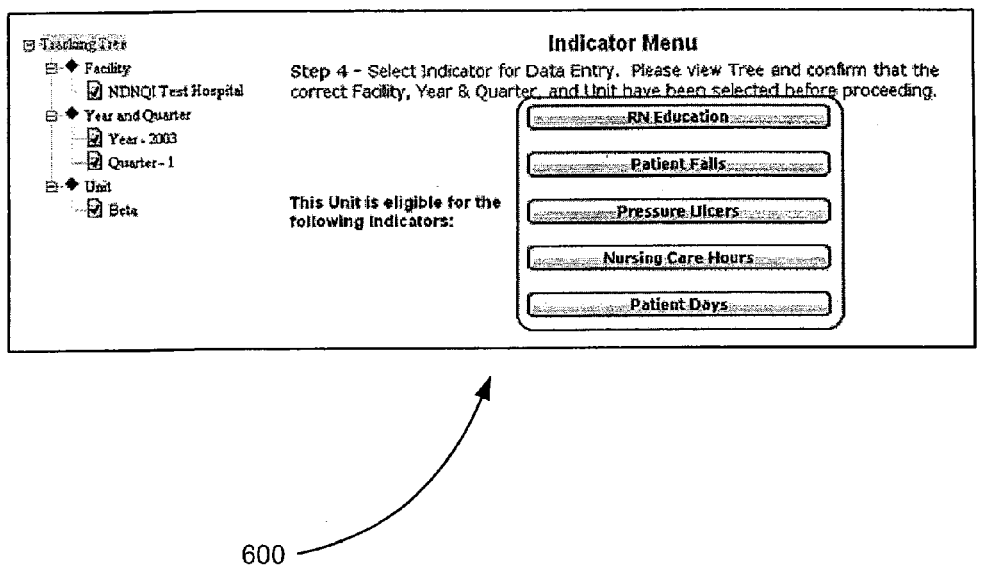
FIG. 6 is an exemplary Web page of an exemplary national database of a nursing quality indicators system used to chooses a category of nursing quality indicators, in accordance with an embodiment of the present invention.

FIG. 6 is an exemplary Web page 600 of an exemplary NDNQI system used to chooses a category of nursing quality indicators, in accordance with an embodiment of the present invention. After selecting a nursing unit, a user chooses a category of nursing quality indicators, or a module. Exemplary modules include a "general overview" module, a "patient falls" module, a "nursing care hours" module, a "patient days" module, a "pressure ulcer survey" module, and an "RN education" module. Patient falls, nursing care hours, patient days, and the pressure ulcer survey are quarterly indicators. In other words, data entered for these modules should be submitted quarterly.

Figure 7:
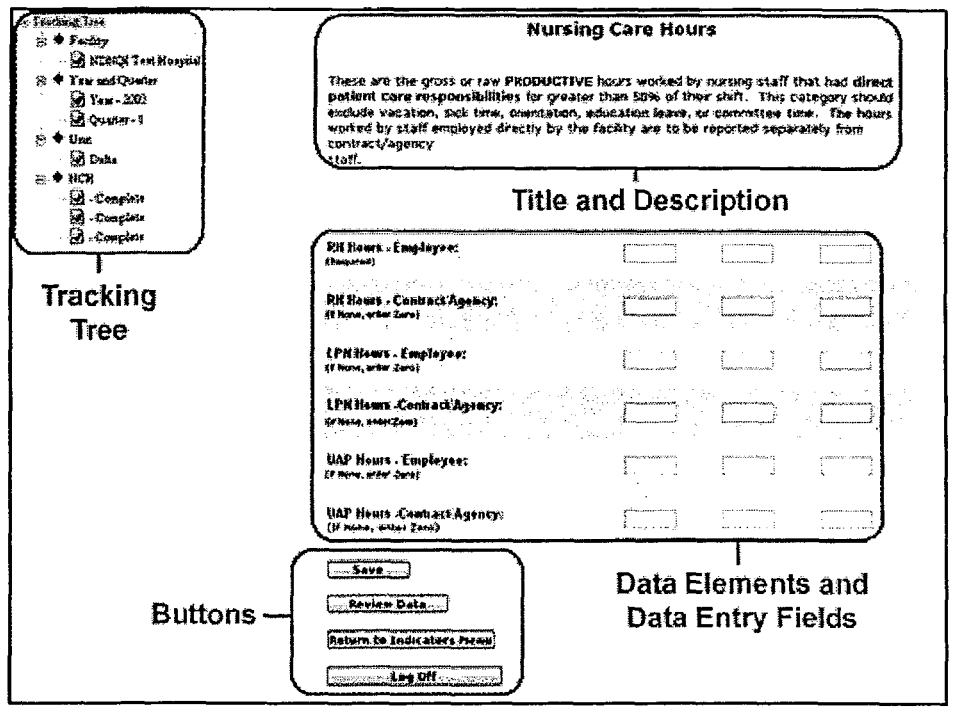
FIG. 7 is an exemplary Web page of an exemplary national database of a nursing quality indicators system used to enter nursing care hours information, in accordance with an embodiment of the present invention.

FIG. 7 is an exemplary Web page 700 of an exemplary NDNQI system used to enter nursing care hours information, in accordance with an embodiment of the present invention. The title and description, tracking tree, data elements and entry fields, and buttons are shown circled on Web page 700. In a preferred embodiment, each module contains a data entry page, which contains a title and brief description of data to be entered, a tracking tree, data elements and data entry fields, and buttons to save data, select another module, review data entry, or to log off. A tracking tree graphically displays the information that has been saved on the selected nursing unit and module. A user can return to menus or to a previous entry for editing by simply clicking on that particular entry on the tracking tree. Some data entry fields allow text entry, others are drop down menus with specific data points.

After data has been entered and saved, the data fields are cleared and ready for the next set of data, if appropriate. For some modules, the data is displayed for review. This is an opportunity to quickly confirm that the saved information is correct. For other indicators the user is directed to a review data button. A user can review data that has been submitted for each module. This report is available for data entered directly into the web site or submitted via XML file format. FIG. 8 is an exemplary Web page 800 of an exemplary NDNQI system used to review nursing care hours information, in accordance with an embodiment of the present invention. The "edit" and "save" buttons of Web page 800 are shown circled.

Figure 9:
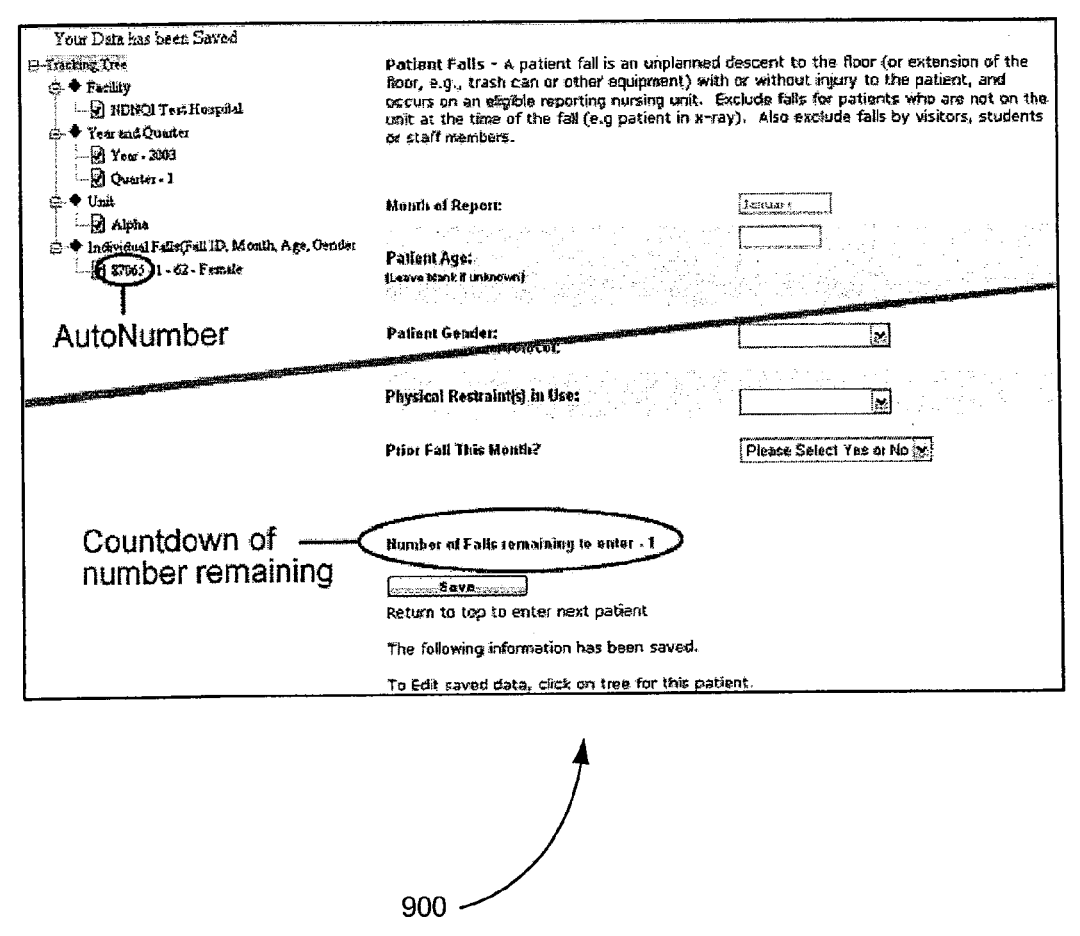

For compliance with HIPAA regulations, each patient for whom data is entered is assigned a computer generated number. After the record is saved, the number is displayed on the tracking tree along with patient age and gender. For those modules that require entering data on individual patients, the screen displays a countdown of the number of patients remaining to be entered. This provides the user with another opportunity to confirm that they have complete data entry. The countdown is based on the number of patients listed on summary or census pages. FIG. 9 is an exemplary Web page 900 of an exemplary NDNQI system showing how a computer generated number and a countdown number are used in a patient falls data entry module, in accordance with an embodiment of the present invention. The computer generated number, or autonumber, and countdown numbers are shown circled on Web page 900.

Since all data, both quarterly indicator and RN satisfaction, are collected and reported by unit type, it is important to correctly designate nursing units. In general, in-patient units with well-defined acuity levels are eligible for quarterly indicators. All unit types, whether in-patient, out-patient, mixed acuity, or other, are eligible for RN satisfaction survey.

Each nursing unit is classified according "name," "patient population," and "unit type." Name is the name routinely used at the healthcare facility for this unit. Patient population is the primary patient population cared for on the unit, excluding overflow. Unit type is the primary unit type, excluding occasional overflow. For example, an adult med-surg unit that occasionally may have a small volume of pediatric or maternity patients may enroll as an adult med-surg unit as long as 90% of the patient population is adult acute care with medical and surgical diagnoses. This designation is the group with which the nursing unit is compared in all reports, both quarterly indicator and RN Satisfaction.

In addition to name, patient population, and unit type, a nursing unit may be assigned a sub specialty. Each unit can have one sub specialty. Selecting a sub specialty is not required and, in many cases is inappropriate. Data can also be compared by sub specialty. A sub specialty designation is appropriate if greater than fifty percent of patient care services are related to the designation category.

The category of step down unit is defined as a nursing unit that provides care to patients requiring a higher level of care than provided on an acute care unit, yet not sufficiently intensive as to require admission to critical care. Examples of step down units would be progressive care or intermediate care. Telemetry does not necessarily indicate acuity level as it may be available on general acute care units.

Units that are designed to care for patients with multiple level of acuities are designated as a mixed acuity type. For example, a unit with four intensive care unit (ICU) beds, six step down beds, and twelve med-surg beds would be considered a mixed acuity unit, even though the patients may all have similar diagnoses or specialty. Another example of a step down unit is a unit that has patients with med-surg acuities and "swing beds" for skilled nursing or hospice patients.

Comparisons are not meaningful for unit types in which staffing and patient acuity are not similar. Mixed acuity units are excluded from quarterly indicators to reduce error in NDNQI database 110, shown in FIG. 1. Correct, consistent unit designation is critical to the foundation of NDNQI database 110. Preferably, unit name, patient population, unit type, or sub specialty cannot be edited once entered. Only the NDNQI project staff can make changes to unit information.

Figure 10:
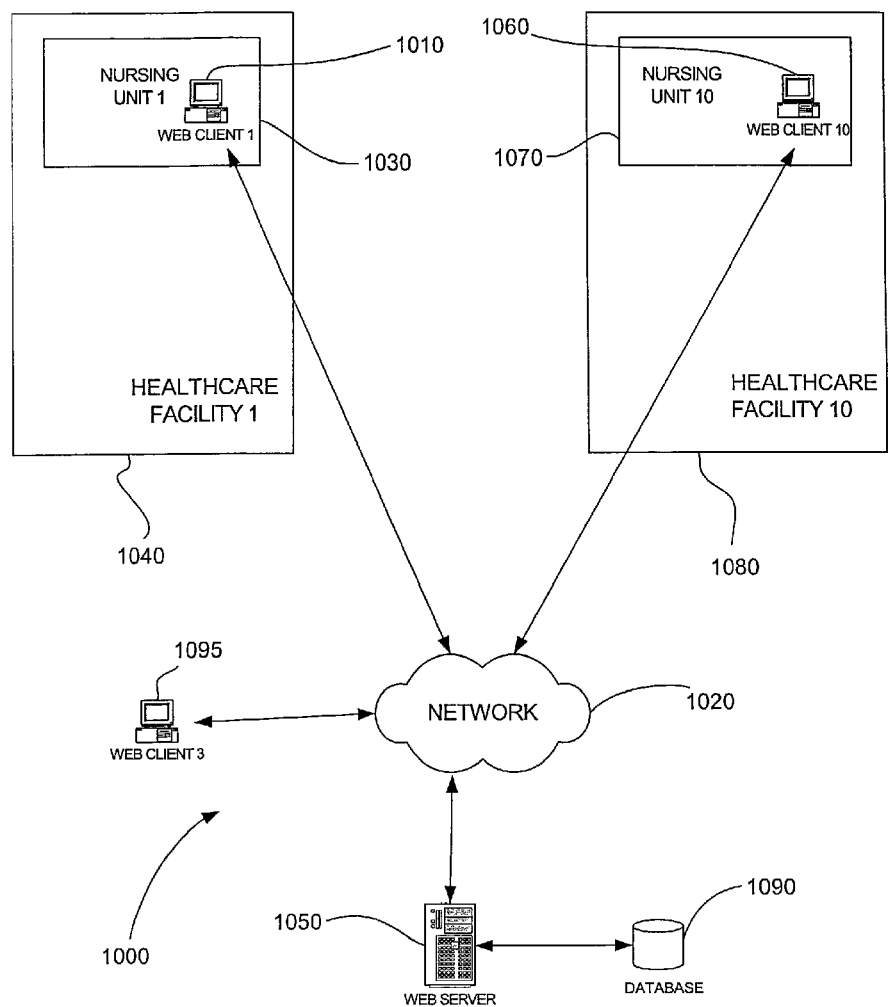
FIG. 10 is a schematic diagram showing a system for surveying nursing quality of nursing units at multiple healthcare facilities connected via a network, in accordance with an embodiment of the present invention.

FIG. 10 is a schematic diagram showing a system 1000 for surveying nursing quality of nursing units at multiple healthcare facilities connected via a network, in accordance with an embodiment of the present invention. First Web client 1010 is connected to network 1020. First Web client 1010 presents a question relating to a nursing quality indicator to a nurse of first nursing unit 1030 of first healthcare facility 1040. First Web client 1010 receives a first answer to the question from the nurse of first nursing unit 1030 of first healthcare facility 1040. First Web client 1010 then transmits a first unit type of first nursing unit 1030, a first identifier of first healthcare facility 1040, and the first answer via network 1020 to Web server 1050.

Second Web client 1060 is also connected to network 1020. Second Web client 1060 presents the same question relating to a nursing quality indicator to a nurse of second nursing unit 1070 of second healthcare facility 1080. Second Web client 1060 receives a second answer to the question from the nurse of second nursing unit 1070 of second healthcare facility 1080. Second Web client 1060 then transmits a second unit type of second nursing unit 1070, a second identifier of second healthcare facility 1080, and the second answer via network 1020 to Web server 1050.

Database 1090 stores the first answer along with the first unit type and the first identifier and stores the second answer along with the second unit type and the second identifier.

Web server 1050 transmits the question to first Web client 1010 and second Web client 1060. Web server 1050 receives the first answer, the first unit type, and the first identifier from first Web client 1010 and receives the second answer, the second unit type, and the second identifier from second Web client 1060. Web server 1050 saves the first answer, the first unit type, the first identifier, the second answer, the second unit type, and the second identifier in database 1090. If the first unit type and the second unit type are substantially the same type, Web server 1050 performs a comparison of the first answer and the second answer stored in database 1090 and lists results of the comparison based on unit type and healthcare facility. Third Web client 1095 receives and displays the results from Web server 1050, if the first unit type and the second unit type are substantially the same type. Third Web client 1095 may be accessible to a site coordinator of first healthcare facility 1040 or second healthcare facility 1080, for example.

Figure 11:
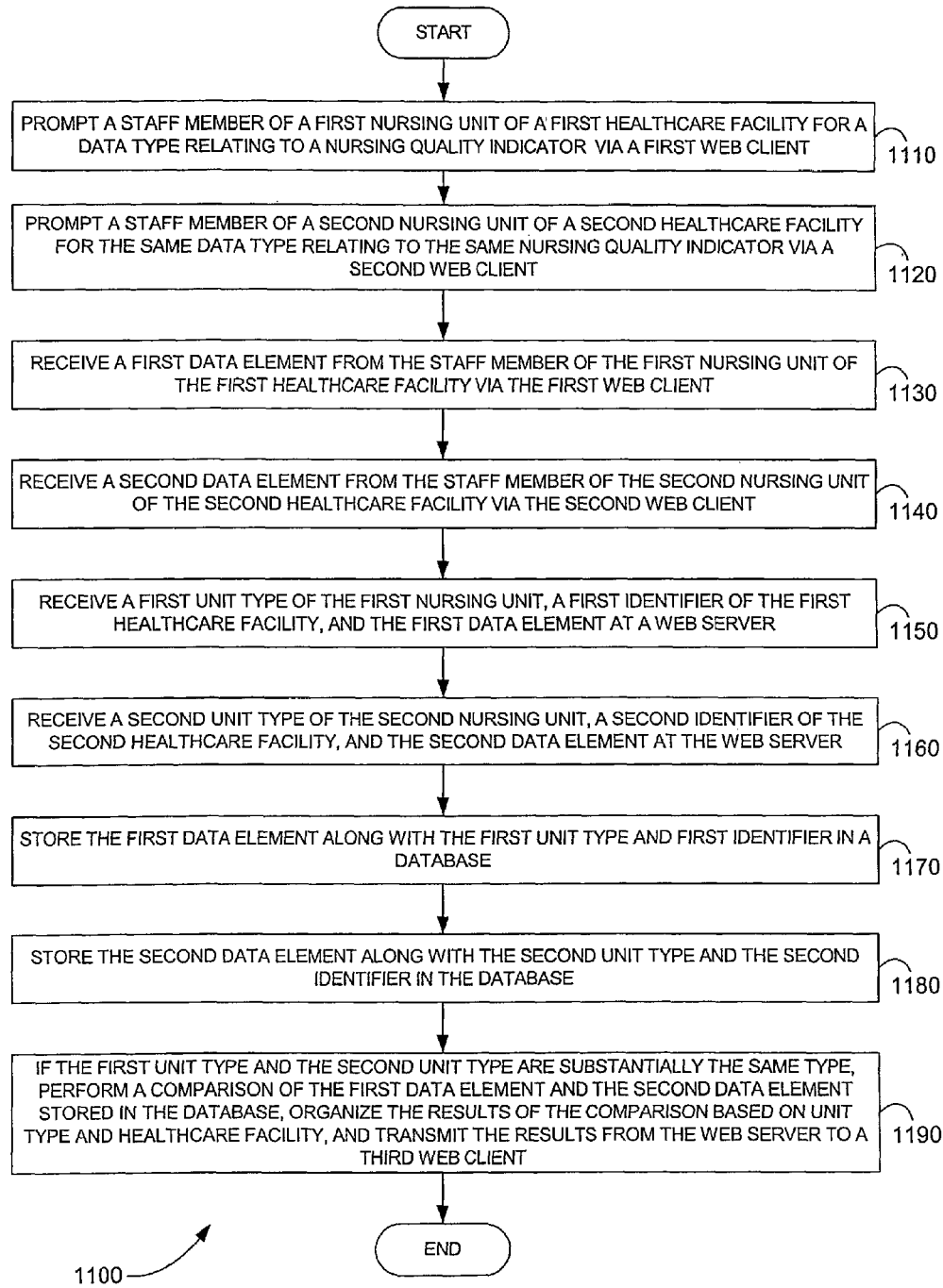
FIG. 11 is a flowchart showing a method for surveying nursing quality of nursing units at multiple healthcare facilities connected via a network, in accordance with an embodiment of the present invention.

FIG. 11 is a flowchart showing a method 1100 for surveying nursing quality of nursing units at multiple healthcare facilities connected via a network, in accordance with an embodiment of the present invention.

In step 1110 of method 1100, a question relating to a nursing quality indicator is presented to a nurse of a first nursing unit of a first healthcare facility via a first Web client connected to the network.

In step 1120, the question is presented to a nurse of a second nursing unit of a second healthcare facility via a second Web client connected to the network.

In step 1130, a first answer to the question is received from the nurse of the first nursing unit via the first Web client.

In step 1140, a second answer to the question is received from the nurse of the second nursing unit via the second Web client.

In step 1150, a first unit type of the first nursing unit, a first identifier of the first healthcare facility, and the first answer are transmitted to a Web server.

In step 1160, second unit type of the second nursing unit, a second identifier of the second healthcare facility, and the second answer are transmitted to the Web server.

In step 1170, the first answer along with the first unit type and the first identifier are stored in a database.

In step 1180, the second answer along with the second unit type and the second identifier are stored in the database.

In step 1190, if the first unit type and the second unit type are substantially the same type, a comparison of the first answer and the second answer stored in the database is performed, the results of the comparison are listed based on unit type and healthcare facility, and the results are transmitted from the Web server to a third Web client for display.

Pediatric Peripheral Intravenous Infiltration Indicators

The term peripheral intravenous (PIV) infiltration is used for both infiltration and extravasation. An intravenous (IV) infiltration is the unplanned administration of a nonvesicant solution or medication into a surrounding tissue. An IV infiltration occurs when the IV access device pulls out of, or pierces the vein. An IV extravasation is the unplanned administration of a vesicant solution or medication into the surrounding tissue. A nonvesicant is defined as an agent that does not cause blistering. A vesicant is an agent capable of causing blistering. A PIV infiltration is an IV infiltration occurring in the peripheral venous system.

One purpose of pediatric PIV indicators is to determine the prevalence of PIVs in hospitalized pediatric and neonatal populations. Another purpose of pediatric PIV indicators is to explore the relationship between nursing staffing and pediatric PIVs. Nurses doing the assessments of pediatric PIV indicators are trained and skilled in assessing and staging IV infiltrations.

The source of pediatric PIV indicator data is a monthly one-day prevalence study on all peripheral IV sites, of all patients receiving either PIV fluids or medications. Previous sites from discontinued IVs are preferably not included.

Patients with saline or heparin locked PIV catheters not receiving either fluids or medications are excluded from the prevalence study. Central venous lines, peripherally inserted central catheters (PICC) lines, and midline catheters are excluded from the prevalence study.

The prevalence study is a cross-sectional count of the number of cases at a specific point in time, or the number of individuals with an IV infiltration who exist in a patient population at a given point in time. This type of study is also called a snap-shot or point prevalence study. PIV infiltration prevalence is calculated by dividing the total number of PIV infiltrations on the nursing unit divided by the total number of PIV sites on the unit. Preferably, PIV infiltrations between grades two and four are included.

On the day of the monthly prevalence study, each peripheral IV site for which a fluid or medication is infusing or has been infused within the last hour must be visually assessed for infiltration. The pediatric PIV indicator requires documentation on all patients with IVs (whether the patient has an infiltration(s) or not), who are on the reporting unit on the designated survey date, in order to calculate a prevalence rate.

Each site and the surrounding tissue is viewed either through a transparent dressing or with the dressing removed. It is not acceptable to substitute other signs for direct observation of the site and surrounding tissue. For example, an IV site can not be assessed as negative for infiltration based solely upon blood return, distal extremity appearance, or temperature, without visualizing the site. In such a case, the dressing must be removed for assessment. For every IV site, the infiltration status is documented. Infiltration status is a required element for reporting. Preferably, up to four IV sites are recorded for a single patient.

Pediatric nursing units typically eligible to collect pediatric PIV infiltration indicator data include critical care, step down, medical, surgical, and medical and surgical combined. Outpatient and mixed acuity pediatric units are typically excluded. Neonatal nursing units typically eligible to collect pediatric PIV infiltration indicator data include critical care (level III) nursery and intermediate care (level II) nursery. Level I nurseries, well baby nurseries, and mixed acuity nurseries are typically excluded.

The pediatric PIV prevalence study consists of a number questions designed to gather information on each pediatric PIV patient. The information gathered includes patient age, patient height, patient weight, patient gender, IV site, agent category, agent description, and extent of patient injury.

The age of each patient is recorded. For pediatric populations the patient age is preferably recorded in years and months. For neonates thirty days old or less than thirty days old, the patient age is preferably recorded in days of life. For neonates greater than thirty days old, the patient age is preferably recorded in months.

The height of each patient is recorded. For both pediatric and neonatal populations the patient height is preferably recorded in centimeters.

The weight of each patient is recorded. For patients up to one thousand grams in weight, patient weight is recorded in grams. For patients weighing one thousand grams or more, patient weight is recorded in kilograms.

The gender of each patient is recorded.

The site of each IV administration is recorded. Preferably, the sites include, scalp, right arm, left arm, right hand, left hand, right leg, left leg, right foot, left foot, and other.

The agent category is recorded. For each infiltration, the infiltrate is preferably categorized as either a vesicant or non-vesicant solution.

The agent description is recorded. For each infiltration, the solution or additive description is preferably crystalloid-no additive, crystalloid-additional electrolytes added, non-blood colloid, blood product, antibiotic, chemotherapeutic agent, vasoconstrictor, other medication, or other solution.

The extent of patient injury is recorded. For each IV site, infiltration injury is preferably recorded as "Grade 1," "Grade 2," "Grade 3," or "Grade 4." IV's without infiltration are preferably recorded as "no infiltration." A "Grade 1" infiltration is defined as blanched skin, edema less than one inch in any direction, and cool to the touch with or without pain. A "Grade 2" infiltration is defined as blanched skin, edema one to six inches in any direction, and cool to the touch. A "Grade 3" infiltration is defined as blanched and translucent skin, gross edema or edema greater than six inches in any direction, mild to moderate pain, possible numbness, and cool to the touch. A "Grade 4" infiltration is defined as blanched, translucent, tight, leaking, discolored, bruised, and swollen skin, circulatory impairment, infiltration of any amount of blood product or vesicant, moderate to severe pain, gross edema or edema greater than six inches in any direction, and deep pitting edema.

PIV infiltration in children age ten years or older is preferably assessed to grade the severity of the tissue injury using the complete intravenous nursing society (INS) infiltration scale. PIV infiltration in children less than ten years of age is assessed using the INS infiltration scale without reference to the size of the tissue involvement. PIV infiltrations of "Grade 1" and "Grade 2" are preferably considered "Grade 2" in children less than ten years of age.

Figure 12:
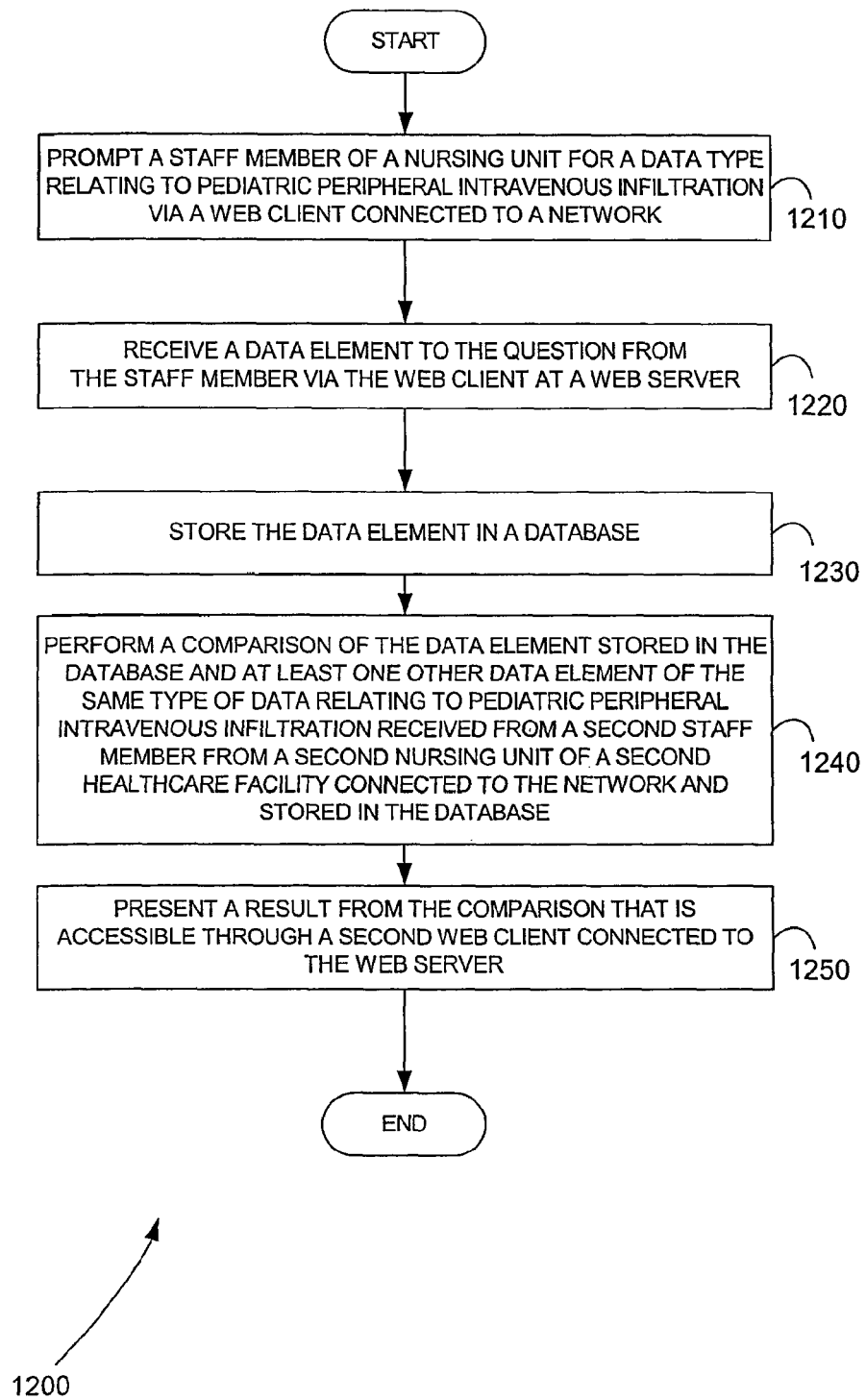
FIG. 12 is a flowchart showing a method for surveying nursing quality of a nursing unit at a healthcare facility connected to a network based on pediatric intravenous infiltration information, in accordance with an embodiment of the present invention.

FIG. 12 is a flowchart showing a method 1200 for surveying nursing quality of a nursing unit at a healthcare facility connected to a network based on pediatric intravenous infiltration information, in accordance with an embodiment of the present invention.

In step 1210 of method 1200, a question relating to a pediatric peripheral intravenous infiltration is presented to a nurse of the nursing unit via a Web client connected to the network.

In step 1220, an answer to the question is received at a Web server from the nurse via the Web client.

In step 1230, the answer is stored in a database.

In step 1240, a comparison of the answer stored in the database and at least one other answer to the question received from a second nurse from a second nursing unit of a second healthcare facility connected to the network and stored in the database is performed.

In step 1250, a result from the comparison is presented that is accessible through a second Web client connected to the Web server.

Pediatric Pain Indicators

Pain assessment is a comprehensive evaluation of pain location, characteristics, onset/duration, frequency, quality, intensity/severity, and precipitating factors. Pain assessment includes observation of behavioral and physiologic signs of discomfort, especially in those unable to communicate. Pain assessment is conducted using a valid, reliable, and age-appropriate instrument.

Pain intervention is the selection and implementation of a variety of measures (e.g. pharmacologic, nonpharmacologic, interpersonal) to facilitate pain relief. The administration of sedatives or hypnotics without analgesia is not considered a pain intervention.

Pain reassessment is the subsequent evaluation of the effectiveness of pain relief measures following the intervention.

Completion of the pain assessment/intervention/reassessment (AIR) cycle is demarcated by documentation in the medical record of pain assessment, pain intervention, and pain reassessment conducted by the professional nurse caring for the pediatric patient.

The purpose of pediatric AIR cycle indicators is three-fold. The first purpose is to determine the prevalence of complete pain AIR cycles in hospitalized pediatric and neonatal populations. The second purpose is to determine the average length of time between pain assessments in the nursing unit. The third purpose is to explore the relationship between the documented pain AIR cycle and nursing hours worked.

The source of data is a quarterly one-day prevalence study including preferably all patients on the unit who have been present on the unit for at least twenty-four hours. All patients regardless of illness acuity, diagnosis, or resuscitation status are included. Patients who are pharmacologically paralyzed or continuously sedated are not excluded.

The pediatric pain prevalence study is a cross-sectional count of the number of cases at a specific point in time, or the number of individuals with completed pain AIR cycles who exist on the patient care unit at a specific point in time. This type of prevalence study is also called a snap-shot or point prevalence study.

Pain AIR cycle prevalence is calculated by dividing the total number of completed cycles by the total number of cycles on the unit. The average time between pain cycles is calculated by dividing the total number of pain assessments for an individual by 24 hours, then adding the patient averages and dividing by the number of patients.

On the day of the quarterly prevalence study, each patient who has been present on the unit for at least 24 hours has the most recent two pain cycles evaluated for completeness. The patient care record is reviewed, and each element of the cycle is addressed and reported. In order to be considered as complete, pain assessment, pain intervention, and pain reassessment must be documented. A reviewer also records the total number of pain assessments documented within the last twenty-four hours for each patient.

Pediatric nursing units typically eligible to collect pediatric PIV infiltration indicator data include critical care, step down, medical, surgical, and medical and surgical combined. Outpatient and mixed acuity pediatric units are typically excluded. Neonatal nursing units typically eligible to collect pediatric PIV infiltration indicator data include critical care (level III) nursery and intermediate Care (level II) nursery. Level I nurseries, well baby nurseries, and mixed acuity nurseries are typically excluded.

The pediatric pain AIR cycle prevalence study consists of a number questions designed to gather information on each pediatric PIV patient. The information gathered includes number of pain assessments per day, patient age, patient height, patient weight, patient gender, pain assessment, pain scale, type of pain, pain intervention, and pain reassessment.

The total number of pain assessments initiated with a patient with a twenty-four hour period are recorded. The pain AIR cycle does not need to be complete in order to be counted.

The age of each patient is recorded. For pediatric populations the patient age is preferably recorded in years and months. For neonates thirty days old or less than thirty days old, the patient age is preferably recorded in days of life. For neonates greater than thirty days old, the patient age is preferably recorded in months.

The height of each patient is recorded. For both pediatric and neonatal populations the patient height is preferably recorded in centimeters.

The weight of each patient is recorded. For patients up to one thousand grams in weight, patient weight is recorded in grams. For patients weighing one thousand grams or more, patient weight is recorded in kilograms.

The gender of each patient is recorded.

The pain assessment of each patient is recorded. The pain assessment is preferably recorded as documentation on the presence of pain, no pain, or sleeping.

The pain scale of each patient is recorded. The pain scale is preferably recorded as the faces scale, the face, legs, activity, cry, and consolability (FLACC) scale, a numeric scale, the oucher scale, a visual analog, the crying, requires oxygen for saturation of greater than ninety-five percent, increased vital signs, expression, and sleeplessness (CRIES) scale, the neonatal pain, agitation, and sedation scale (N-PASS), the neonatal infant pain scale (NIPS), behavioral cues (crying, guarding, frowning, etc.), physiological signs (tachycardia, elevated blood pressure, etc.), or other.

The type of pain experienced by each patient is recorded. The type of pain experienced is preferably recorded as procedural/post-procedural, post-operative, chronic, traumatic, acute disease process, developmental, or other. Procedural/post-procedural pain includes but is not limited to pain from line placement, chest tube placement, fracture reduction, bone marrow aspiration, dressing changes, laceration repair, wound care, and devices. Post-operative pain is pain from a surgical procedure during recovery and convalescence. Chronic is pain from chronic illnesses such as cancer, arthritis, etc. Traumatic pain is pain resulting from traumatic injuries. Acute disease process pain is pain such as headache, sore throat, abdominal pain, pain from sickle cell crisis, or other types of pain which result from an acute illness process. Developmental pain is pain resulting from normal developmental processes such as teething.

The pain intervention performed for each patient is recorded. The pain intervention recorded per pain episode is preferably one or more of pharmacologic, distraction, relaxation, music, guided imagery, repositioning, environmental modification, therapeutic touch, or other.

The pain reassessment for each patient is recorded. The pain reassessment is preferably documentation of whether or not the patient was reassessed for pain following the pain intervention.

Figure 13:
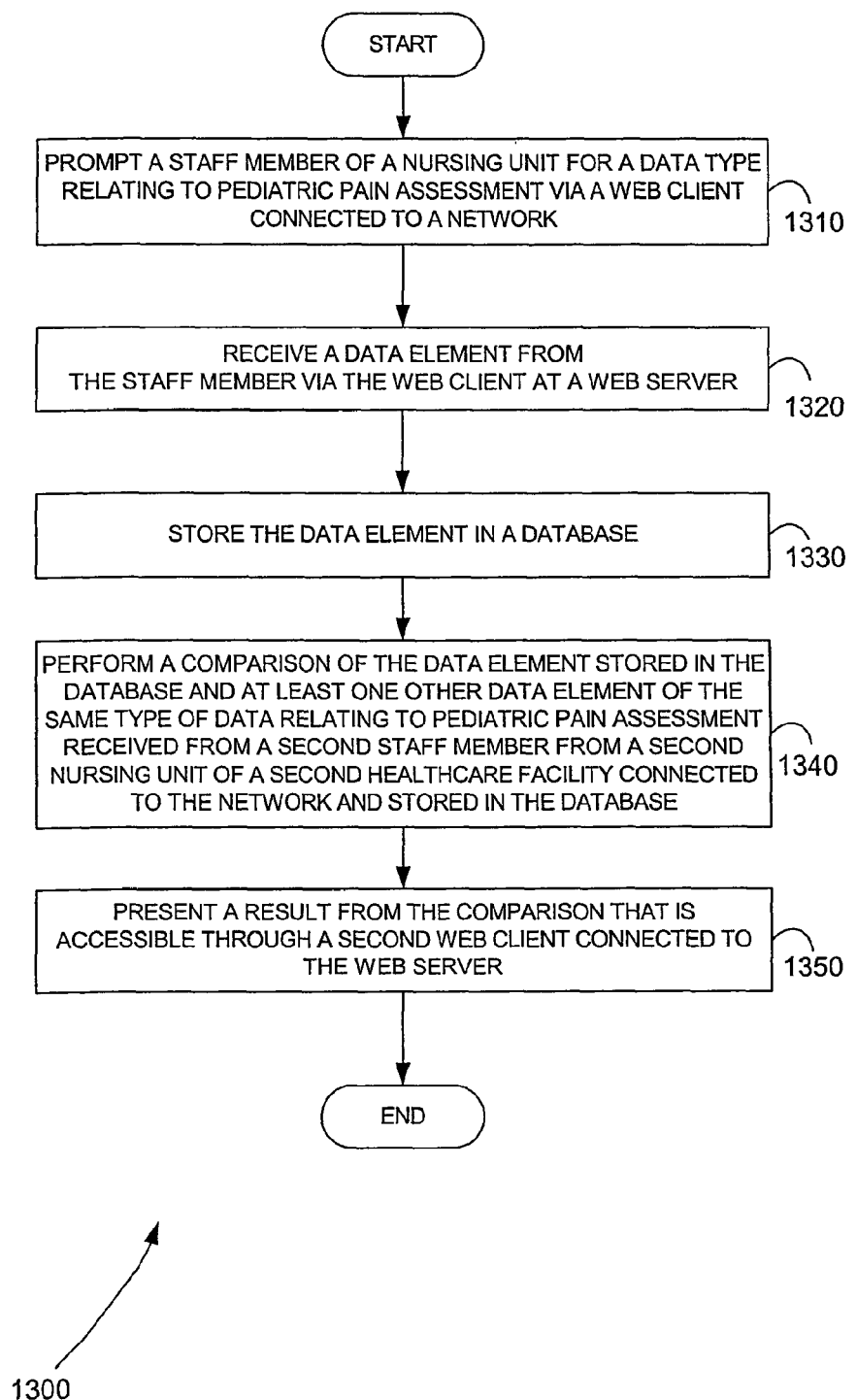
FIG. 13 is a flowchart showing a method for surveying nursing quality of a nursing unit at a healthcare facility connected to a network based on pediatric pain assessment information, in accordance with an embodiment of the present invention.

FIG. 13 is a flowchart showing a method 1300 for surveying nursing quality of a nursing unit at a healthcare facility connected to a network based on pediatric pain assessment information, in accordance with an embodiment of the present invention.

In step 1310 of method 1300, a question relating to a pediatric pain assessment is presented to a nurse of the nursing unit via a Web client connected to the network.

In step 1320, an answer to the question is received at a Web server from the nurse via the Web client.

In step 1330, the answer is stored in a database.

In step 1340, a comparison of the answer stored in the database and at least one other answer to the question received from a second nurse from a second nursing unit of a second healthcare facility connected to the network and stored in the database is performed.

In step 1350, a result from the comparison is presented that is accessible through a second Web client connected to the Web server.

Physical and Sexual Assault Indicators

Assaults are unwanted contact with another person with intent to harm. The contact may or may not result in injury. Physical assaults involve the use of force and include punching, kicking, slapping, biting, spitting, and throwing objects directly at another person. Sexual assaults are unwanted sexual contacts and include rape, attempted rape, fondling, forced kissing, and exposure. The definitions do not include verbal threats or nonverbal intimidation. The behaviors involve the use of force and can be directed at staff members, students, other patients, or visitors.

The physical and sexual assault indicators record assaultive behavior performed by patients. Assaultive behaviors demonstrated by visitors, students, staff members, patients on units not eligible for reporting, and patients on units eligible for reporting unit, however patient was not on unit at time of the assaultive behavior (e.g., patient assaultive episode occurred in recreational therapy activity) are excluded.

The purposes of the physical and sexual assault indicators are to determine the rates of physical and sexual assaults in psychiatric inpatient settings, determine the frequency with which these assaults result in injury, and explore the relationship between assaultive episodes and nursing staffing.

An eligible reporting unit reports episodes of assaultive behavior by patients by calendar month. In addition, each unit that reports data on patient assaults also submits patient data daily for the same month, in order to have assault rates calculated.

Physical and sexual assault indicator data comes from secondary risk management sources (incident reports, variance reports, event reports, etc.) that are completed by the nursing staff either on paper or electronically. Therefore any event related to an act of assault by a patient that occurs on an eligible reporting unit and generates a report is counted.

Physical and sexual assault indicator data consists of summary and patient data. Summary data is reported monthly for a nursing unit. Patient data is reported per patient per episode of assaultive behavior.

Both summary and patient data are collected from responses to questions posed to nursing staff. The summary data collected from responses to questions includes month of report, nursing unit type, indicator of whether nursing unit is locked, type of healthcare facility, frequency of nursing staff assault management training, and number of monthly assaultive episodes. The patient data collected from responses to questions includes patient age, patient gender, status of patient's admission, p, time since patient admission, type of assault, whether a previous assault occurred during the month, automatically generated identifier of the first assault occurring during the month, number of victims, type of victims, severity of injuries, nursing credentials of nurse victim, experience of nurse victim, assault management training of nurse victim, assault management training program taken by nurse victim, intervention employed, restraints use, and duration of seclusion and restraint of patient.

The month of the assaultive report is recorded.

The type of nursing unit is recorded. The type of nursing unit recorded is preferably adult, geripsych, child, adolescent, child/adolescent, behavioral health, specialty, and multiple unit type. An adult unit is a unit designated for the care of adult patients with acute psychiatric disorders. A geripsych unit is a unit designated for the care of elderly patients with acute psychiatric disorders. A child unit is a unit designated for the care of children, predominantly ages 2-11 years old, with acute psychiatric disorders. An adolescent unit is a unit designated for the care of adolescents, predominantly ages 12-18 years old, with acute psychiatric disorders. A child/adolescent unit is a unit designated for the care of children and adolescents, predominantly ages 2-18 years old, with acute psychiatric disorders. A behavioral health unit is a unit designated for the care of individuals with eating disorders or a substance abuse diagnosis (including substance abuse rehabilitation). Substance abuse encompasses both alcohol and drugs. Persons of all ages may be in a behavioral health unit. A specialty unit is a unit designated for the care of patients with dual diagnoses (e.g., mental illness and mental retardation, or substance abuse and an additional mental illness diagnosis). Persons of all ages may be in a specialty unit. A multiple unit type is a unit designated for the care of patients that encompass three or more of the above unit types, but for which no one unit type comprises greater than 50% of the entire unit. An indicator of whether nursing unit is locked is recorded. Nursing units are preferably recorded as locked or unlocked.

The type of healthcare facility is recorded. The type of healthcare facility recorded is preferably general acute care hospital, psychiatric hospital, or other.

The frequency of nursing staff assault management training is recorded. The frequency of nursing staff assault management training is preferably the years in assault management training is required to be completed by each nursing staff member. The frequency of nursing staff assault management training is preferably left blank if the nursing unit does not have a requirement.

The number of monthly assaultive episodes is recorded. The number of monthly assaultive episodes is preferably the number of assaultive episodes occurring in the nursing unit within the calendar month.

The age of the assaultive patient is recorded. The patient age is preferably the patient's age on their last birthday. For HIPAA compliance, ninety is entered for any age that is ninety or greater.

The gender of the assaultive patient is recorded. The patient gender is preferably recorded as male, female, or "no documentation." "No documentation" is entered if the data is obtained from a secondary source and there is no documentation of gender.

The time since the admission of the assaultive patient is recorded. The time since patient admission is preferably recorded as the hours or days between the patient's admission to the unit and the assault. The time since patient admission is recorded as no documentation if the data is entered from a secondary source and there is no documentation of time since admission.

The type of assault is recorded. Assault includes both physical and sexual assaults. The type of assault recorded is preferably physical, sexual, both physical and sexual, or no documentation.

Whether a previous assault occurred during the month is recorded. More than one episode of assault by the same patient after the current admission to the nursing unit is classified as a repeat assault. Patients who assault someone elsewhere prior to admission to the unit (in the emergency department, for example) or on a prior admission are not classified as a repeat assault. A repeat assault is operationally defined to occur if a second (or subsequent) incident report is completed. Whether a previous assault occurred during the month is preferably recorded as no, if this was the first time this patient exhibited assaultive behavior after admission to the nursing unit during the current calendar month, and yes, if the current assault is a repeat assault since admission during the current calendar month. Whether a previous assault occurred during the month is preferably recorded as no documentation, if the data is entered from a secondary source and there is no documentation of prior assaultive behavior.

The automatically generated identifier of the first assault occurring during the month. When an individual patient data record is saved, a random identifier is automatically generated to protect the identity of the patient and comply with HIPAA regulations. If patient committed a previous assault during the current month, the automatically generated identifier of the first previous assault record is recorded.

The number of victims is recorded. An assaultive episode can involve one or more victims. The number of victims is preferably the number of persons that were either targets of the assault or who became targets during the assaultive episode. If the patient exhibited self-destructive behaviors, the patient is not included in the total number of victims. The number of victims is recorded as "no documentation" if the data is entered from a secondary source and there is no documentation regarding the number of victims of the assault.

The type of victims is recorded. The type of victims is preferably recorded as nursing staff member, physician, other healthcare provider, resident/intern, student, another patient, visitor of patient, visitor of another patient, employees other than healthcare providers, other, or no documentation.

The severity of injuries is recorded. The injuries that are being judged are physical injuries. The severity of injuries is preferably recorded as none, minor, moderate, major, death, or no documentation.

The nursing credentials of the nurse victim are recorded. The highest credentials of the nurse victim are preferably recorded as advance practical nurse, registered nurse, licensed practical or vocational nurse, licensed mental health technician, unlicensed assistive personnel, or no documentation.

The experience of the nurse victim is recorded. The experience of the nurse victim is preferably the number of years of psychiatric nursing experience of the nursing staff member who was the most seriously injured victim of assault. The experience of the nurse victim includes years of psychiatric work experience at the current institution as well as previous psychiatric experience in a similar position at other psychiatric units or institutions. The experience of the nurse victim is preferably recorded as no documentation if the data is entered from a secondary source and there is no documentation of the years of experience of the victim of assault.

The assault management training of the nurse victim is recorded. The assault management training of the nurse victim is preferably recorded as yes, if the most seriously injured nursing staff member who was the victim of assault attended an assault management training program. The assault management training of the nurse victim is preferably recorded as no, if the most seriously injured nursing staff member who was the victim of assault did not attend an assault management training program. The assault management training of the nurse victim is preferably recorded as no documentation if the data is entered from a secondary source and there is no documentation of assault management training of the victim of assault.

The intervention employed is recorded. The type of intervention employed by staff to stop the assaultive behavior is preferably recorded as none because help was unavailable, none for reasons other than the unavailability of help, administered pharmacological agent, calmly talked to patient, verbally instructed patient to leave the immediate environment (i.e., for time out), physically escorted patient from immediate environment, held with force, placed in seclusion (isolation with locked door), applied restraints, other and please note, or no documentation.

The restraints employed are recorded. Restraints are any physical or chemical way to stop a patient from being free to move. Restraints are used to prevent patient injury and are not used for treating medical symptoms. The restraints employed are preferably recorded as no restraints were used, vest (posey), blanket wraps, papooses, net restraints, wrist-waist, four-point, five-point, chemical, or no documentation.

The duration of restraint is recorded. Time is recorded in minutes, hours, and days.

The duration of seclusion is recorded. Seclusion is defined as the involuntary confinement of a patient in a room or an area where the person is physically prevented from leaving. Seclusion involves not only the act of confining an individual to an area, but also separating him or her from others. The duration of seclusion is preferably recorded in minutes or as no documentation if the data is entered from a secondary source and there is no documentation of seclusion.

Figure 14:
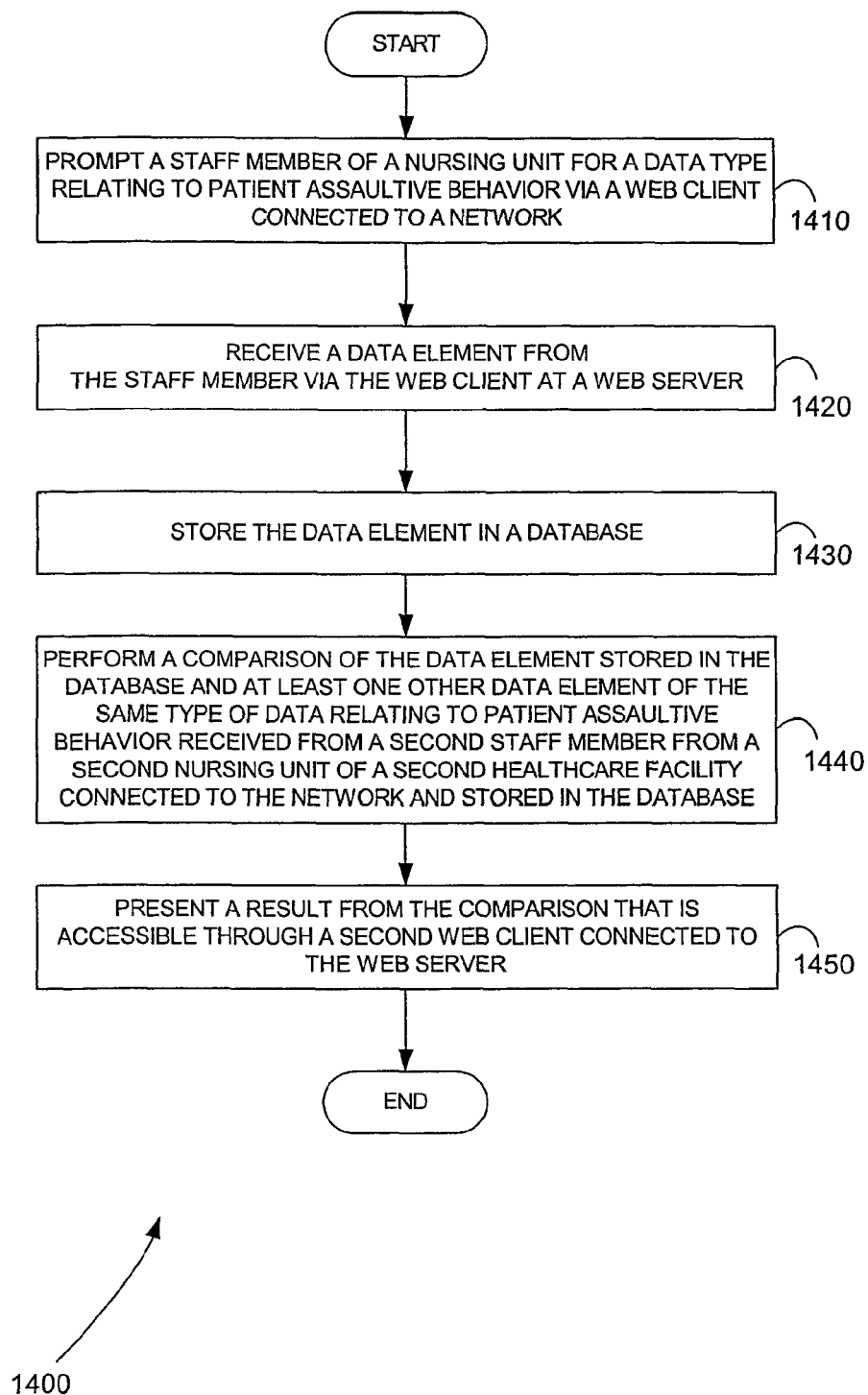
FIG. 14 is a flowchart showing a method for surveying nursing quality of a nursing unit at a healthcare facility connected to a network based on patient assaultive behavior information, in accordance with an embodiment of the present invention.

FIG. 14 is a flowchart showing a method 1400 for surveying nursing quality of a nursing unit at a healthcare facility connected to a network based on patient assaultive behavior information, in accordance with an embodiment of the present invention.

In step 1410 of method 1400, a question relating to patient assaultive behavior is presented to a nurse of the nursing unit via a Web client connected to the network.

In step 1420, an answer to the question is received at a Web server from the nurse via the Web client.

In step 1430, the answer is stored in a database.

In step 1440, a comparison of the answer stored in the database and at least one other answer to the question received from a second nurse from a second nursing unit of a second healthcare facility connected to the network and stored in the database is performed.

In step 1450, a result from the comparison is presented that is accessible through a second Web client connected to the Web server.

In accordance with an embodiment of the present invention, instructions configured to be executed by a processor to perform a method are stored on a computer-readable medium. The computer-readable medium can be a device that stores digital information. For example, a computer-readable medium includes a compact disc read-only memory (CD-ROM) as is known in the art for storing software. The computer-readable medium is accessed by a processor suitable for executing instructions configured to be executed. The terms "instructions configured to be executed" and "instructions to be executed" are meant to encompass any instructions that are ready to be executed in their present form (e.g., machine code) by a processor, or require further manipulation (e.g., compilation, decryption, or provided with an access code, etc.) to be ready to be executed by a processor.

Systems and methods in accordance with an embodiment of the present invention disclosed herein can advantageously improve nursing quality. Systems and methods for surveying and reporting on nursing quality of nursing units at multiple facilities across the nation connected via a network enable healthcare facilities to monitor their nursing quality indicators with patient outcomes in a nationwide, longitudinal framework. In addition, systems and methods for surveying nursing quality of nursing units at multiple facilities connected via a network enable the creation of new indicators or the refinement of existing indicators that can be shared by multiple healthcare facilities across the country.

The foregoing disclosure of the preferred embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as particular sequences of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A system for providing comparative reports regarding nursing quality of nursing units at multiple healthcare facilities, comprising:
   a database configured to store information received from multiple healthcare facilities;
   a computer configured to analyze the information received from multiple healthcare facilities, the computer operable to be in communication with the database;
   a web server operable to be in communication with the database, the web server configured to:
      receive first data, the first data including at least a first answer to a question relating to a nursing quality indicator and a first unit type associated with the first healthcare facility; and
      transmit the first data to the database;
      receive second data, the second data including at least a second answer to a question relating to a nursing quality indicator and a second unit type associated with the second healthcare facility; and
      transmit the second data to the database;
   wherein the database is configured to:
      receive the first data and second data; and
      store the first data and the second data, and
   wherein, when the first unit type of the first data is a same type as the second unit type of the second data, the computer is configured to:
      perform statistical analysis on the first data and the second data; and
      output results of the statistical analysis.

2. The system of claim 1, wherein, when the computer is configured to perform statistical analysis on the first data and the second data, the computer is configured perform statistical analysis on the first answer associated with the first healthcare facility and the second answer associated with the second healthcare facility.

3. The system of claim 1, wherein the nursing quality indicator comprises one or more of: patient falls, nursing care hours, patient days, pressure ulcers, and registered nurse education.

4. The system of claim 1,
wherein the first data further includes information regarding a first number of beds associated with the first healthcare facility and the second data further includes information regarding a second number of beds associated with the second healthcare facility, and
wherein, when the computer is configured to perform statistical analysis on the first data and the second data, the computer is configured to perform statistical analysis of the first answer, the first number of beds associated with the first healthcare facility, the second answer and the second number of beds associated with the second healthcare facility.

5. The system of claim 4, wherein when the computer is configured to output results of the statistical analysis, the computer is configured to organize the output of the results based on a number of beds associated with a healthcare facility.

6. The system of claim 1, wherein the web server is configured to restrict receipt of data to authorized users.

7. The system of claim 1,
wherein the first unit type comprises one or more of: name, patient population, type, and sub-specialty, and
wherein the second unit type comprises one or more of: name, patient population, type, and sub-specialty.

8. The system of claim 1, further comprising an access regulator, the access regulator configured to prevent the receipt of the first data when access requirements have not been met.

9. The system of claim 8, wherein the access requirements comprise the receipt of one or more correct answers to a respective one or more queries, and
wherein the access requirements are met when the system has received a correct answer to each of the one or more queries.

10. A system for providing comparative reports regarding nursing quality of nursing units at multiple healthcare facilities, comprising:
means for storing information received from multiple healthcare facilities;
means for analyzing the information received from multiple healthcare facilities;
means for receiving first data associated with a first healthcare facility, the first data including at least a first answer from a first user to a question relating to a nursing quality indicator and a first unit type;
means for transmitting the first data to the database;
means for storing the first data in the database;
means for receiving second data associated with a second healthcare facility, the second data including at least a second answer from a second user to a question relating to a nursing quality indicator and a second unit type;
means for transmitting the second data to the database;
means for storing the second data in the database;
wherein, when the first unit type of the first data is a same type as the second unit type of the second data, the means for analyzing comprises:
means for performing statistical analysis on the first data and the second data; and
means for outputting results of the statistical analysis.

11. The system of claim 10, wherein means for performing statistical analysis on the first data and the second data comprises means for performing statistical analysis on the first answer associated with the first healthcare facility and the second answer associated with the second healthcare facility.

12. The system of claim 10, wherein the nursing quality indicator comprises one of: patient falls, nursing care hours, patient days, pressure ulcers, and registered nurse education.

13. The system of claim 10,
wherein the first data further includes information regarding a first number of beds associated with the first healthcare facility and the second data further includes information regarding a second number of beds associated with the second healthcare facility, and
wherein means for performing statistical analysis on the first data and the second data comprises means for performing statistical analysis of the first answer, the first number of beds associated with the first healthcare facility, the second answer and the second number of beds associated with the second healthcare facility.

14. The system of claim 13, wherein means for outputting results of the statistical analysis comprises means for organizing the output of the results based on a number of beds associated with a healthcare facility.

15. The system of claim 10, wherein the web server is configured to restrict receipt of data to authorized users.

16. The system of claim 10,
wherein the first unit type comprises one or more of: name, patient population, type, and sub-specialty, and
wherein the second unit type comprises one or more of: name, patient population, type, and sub-specialty.

17. The system of claim 10, further comprising means for regulating access, wherein the means for regulating access comprises means for preventing the receipt of the first data when access requirements have not been met.

18. The system of claim 17, wherein the access requirements comprise the receipt of one or more correct answers to a respective one or more queries, and
wherein the access requirements are met when the system has received a correct answer to each of the one or more queries.

19. A method for providing comparative reports regarding nursing quality of nursing units at multiple healthcare facilities, comprising:
storing information received from multiple healthcare facilities;
analyzing the information received from multiple healthcare facilities;
obtaining first data associated with a first healthcare facility, the first data including at least a first answer to a question relating to a nursing quality indicator from a first user and a first unit type associated with the first healthcare facility;
transmitting the first data to the database;
storing the first data in the database;
obtaining second data associated with a second healthcare facility, the second data including at least a second answer to a question relating to a nursing quality indicator from a second user and a second unit type associated with the second healthcare facility;
transmitting the second data to the database;
storing the second data in the database;
when the first unit type of the first data is a same type as the second unit type of the second data:
performing statistical analysis on the first data and the second data; and
outputting results of the statistical analysis.

20. The method of claim 19, wherein said performing statistical analysis on the first data and the second data comprises performing statistical analysis on the first answer associated with the first healthcare facility and the second answer associated with the second healthcare facility.

21. The method of claim 19, wherein the nursing quality indicator comprises one of: patient falls, nursing care hours, patient days, pressure ulcers, and registered nurse education.

22. The method of claim 19,
wherein the first data further includes information regarding a first number of beds associated with the first healthcare facility and the second data further includes information regarding a second number of beds associated with the second healthcare facility, and
wherein said performing statistical analysis on the first data and the second data comprises performing statistical analysis of the first answer, the first number of beds associated with the first healthcare facility, the second answer and the second number of beds associated with the second healthcare facility.

23. The method of claim 22, wherein said outputting results of the statistical analysis comprises organizing the output of the results based on a number of beds associated with a healthcare facility.

24. The method of claim 19, further comprising:
restricting receipt of data to authorized users.

25. The method of claim 19,
wherein the first unit type comprises one or more of: name, patient population, type, and sub-specialty, and
wherein the second unit type comprises one or more of: name, patient population, type, and sub-specialty.

26. The method of claim 19, further comprising:
preventing the receipt of the first data when access requirements have not been met.

27. The method of claim 26, wherein the access requirements comprise the receipt of one or more correct answers to a respective one or more queries, and
wherein the access requirements are met when the system has received a correct answer to each of the one or more queries.

* * * * *